(12) United States Patent
Gu et al.

(10) Patent No.: US 11,384,287 B2
(45) Date of Patent: Jul. 12, 2022

(54) SIDE CHAIN LIQUID CRYSTAL EPOXY MONOMER (S-LCEM) AND PREPARATION METHOD THEREOF, AND SIDE CHAIN LIQUID CRYSTAL EPOXY RESIN (S-LCER) WITH HIGH INTRINSIC THERMAL CONDUCTIVITY

(71) Applicant: Northwestern Polytechnical University, Xi'an (CN)

(72) Inventors: Junwei Gu, Xi'an (CN); Xutong Yang, Xi'an (CN); Dong Yang, Xi'an (CN); Xiao Zhong, Xi'an (CN); Yongqiang Guo, Xi'an (CN)

(73) Assignee: Northwestern Polytechnical University, Xi'an (CN)

( * ) Notice: Subject to any disclaimer, the term of this patent is extended or adjusted under 35 U.S.C. 154(b) by 0 days.

(21) Appl. No.: 17/174,043

(22) Filed: Feb. 11, 2021

(65) Prior Publication Data

US 2021/0246372 A1    Aug. 12, 2021

(30) Foreign Application Priority Data

Feb. 11, 2020   (CN) .......................... 202010086226.3

(51) Int. Cl.
*C08L 63/00*    (2006.01)
*C09K 19/38*   (2006.01)
*C08K 5/00*     (2006.01)
*C08K 5/17*     (2006.01)
*C09K 19/12*   (2006.01)

(52) U.S. Cl.
CPC .......... *C09K 19/388* (2013.01); *C08K 5/0025* (2013.01); *C08K 5/17* (2013.01); *C09K 19/12* (2013.01); *C09K 2019/122* (2013.01)

(58) Field of Classification Search
CPC ................. C09K 19/388; C09K 19/12; C09K 2019/122; C09K 2019/0429; C07D 303/02; C08L 63/00
See application file for complete search history.

(56) References Cited

U.S. PATENT DOCUMENTS

2021/0246372 A1 * 8/2021 Gu ....................... C07D 303/40

FOREIGN PATENT DOCUMENTS

CN           101195701 B   * 9/2010   ............ C08L 63/00

* cited by examiner

*Primary Examiner* — Geraldina Visconti
(74) *Attorney, Agent, or Firm* — Ray Quinney & Nebeker P.C.; Paul N. Taylor (57) ABSTRACT

The present disclosure provides a side chain liquid crystal epoxy monomer (S-LCEM) and a preparation method thereof, and a side chain liquid crystal epoxy resin (S-LCER) with high intrinsic thermal conductivity, and belongs to the technical field of epoxy resin materials. There are biphenyl mesogenic groups with strong rigidity in a molecular structure of the S-LCEM provided in the present disclosure and there are also flexible connections among chain segments, which promotes the ordered arrangement of S-LCEM molecular chains during a curing process. The highly-ordered arrangement of such mesogenic units is conducive to the formation of a local crystalloid structure, so that a heat flow is transferred along a direction of the ordered molecular chain, which effectively inhibits the scattering of phonons in the S-LCER with high intrinsic thermal conductivity and greatly improves the intrinsic thermal conductivity of the S-LCER with high intrinsic thermal conductivity.

11 Claims, 4 Drawing Sheets

SIDE CHAIN LIQUID CRYSTAL EPOXY MONOMER (S-LCEM) AND PREPARATION METHOD THEREOF, AND SIDE CHAIN LIQUID CRYSTAL EPOXY RESIN (S-LCER) WITH HIGH INTRINSIC THERMAL CONDUCTIVITY

TECHNICAL FIELD

The present disclosure relates to the technical field of epoxy resin materials, and in particular to a side chain liquid crystal epoxy monomer (S-LCEM) and a preparation method thereof, and a side chain liquid crystal epoxy resin (S-LCER) with high intrinsic thermal conductivity.

BACKGROUND

Epoxy resin requires only a simple processing technology and shows excellent dielectric properties and heat resistance, which is widely used in the fields of electronics, electrical appliances, electric motors, and the like. From tiny electronic components to large-capacity generators and motors, and from low and medium voltage distribution networks to high and ultra-high voltage power transmission systems, epoxy resin is used as an insulation system. With the development of electrical equipment towards high voltage and large capacity, the heat quantity per unit volume of the equipment increases sharply. Excessive heat accumulation will accelerate the aging of epoxy resin, destroy an internal structure of epoxy resin, change basic physical and chemical properties of epoxy resin, and affect the quality stability of epoxy resin, thereby greatly shortening a service life of epoxy resin. Therefore, improving the thermal conductivity of an epoxy resin material is of great significance to ensure the safe and stable operation of an electric power system.

Thermally conductive epoxy resin matrix and composites thereof can be divided into two types according to the preparation process: filled type and intrinsic type. A filled epoxy resin-based thermally conductive composite is prepared by filling an epoxy resin matrix with carbon materials exhibiting high thermal conductivity, metals or inorganic fillers, melting, and blending and compounding solutions or powders. However, it is usually necessary to add a large amount of thermally conductive filler to give an epoxy resin-based composite high thermal conductivity, which inevitably leads to drastic deterioration of mechanical properties. At present, there are few research findings on intrinsic thermally conductive epoxy resin matrix, and no ideal intrinsic epoxy resin with high thermal conductivity has been prepared.

SUMMARY

In view of this, the present disclosure is intended to provide an S-LCEM and a preparation method thereof, and an S-LCER with high intrinsic thermal conductivity. The S-LCEM provided in the present disclosure has high thermal conductivity and prominent mechanical properties.

To achieve the above objective, the present disclosure provides the following technical solutions.

The present disclosure provides an S-LCEM with a structure shown in formula I:

formula I

The present disclosure provides a method for preparing the S-LCEM according to the above technical solution, including the following steps:

mixing a compound $P_1$, 4-phenylphenol, a dehydrating agent, 4-dimethylaminopyridine (DMAP), and an organic solvent, and subjecting a resulting mixture to esterification to obtain a compound $P_2$;

mixing the compound $P_2$ with Amberlite IR-120 H ion-exchange resin and an organic solvent, and subjecting a resulting mixture to a first substitution reaction to obtain a compound $P_3$; and mixing the compound $P_3$ with epichlorohydrin (ECH) and triethylamine (TEA), and subjecting a resulting mixture to a second substitution reaction to obtain the S-LCEM; where, the compounds $P_1$, $P_2$, and $P_3$ have structural formulas as follows:

Compound $P_1$

Compound $P_2$

Compound $P_3$

Preferably, the compound $P_1$, 4-phenylphenol, dehydrating agent, and DMAP may have a molar ratio of 1:(0.8-1.0):(0.8-1.0):(0.008-0.01).

Preferably, the esterification may be conducted at 20° C. to 25° C. for 10 h to 12 h.

Preferably, the compound $P_2$ and the Amberlite IR-120 H ion-exchange resin may have a mass ratio of 1:(0.4-0.5).

Preferably, the first substitution reaction may be conducted at 20° C. to 25° C. for 10 h to 12 h.

Preferably, the compound $P_3$, ECH, and TEA may have a molar ratio of 1:(15-20):(2.5-3.0).

Preferably, the second substitution reaction may be conducted at 20° C. to 25° C. for 3 h to 5 h.

The present disclosure also provides an S-LCER with high intrinsic thermal conductivity prepared by subjecting a mixture of an S-LCEM and an amine curing agent to curing reaction, where, the S-LCEM is the S-LCEM according to the above technical solution or an S-LCEM prepared by the preparation method according to the above technical solution; and the liquid crystal epoxy monomer and the amine curing agent have a molar ratio of 2:(1.0-1.2).

The present disclosure provides an S-LCEM with a structure shown in formula I:

formula I

There are biphenyl mesogenic groups with strong rigidity in a molecular structure of the S-LCEM provided in the present disclosure and there are also flexible connections among chain segments, which promotes the ordered arrangement of S-LCEM molecular chains during a curing process. The highly-ordered arrangement of such mesogenic units is conducive to the formation of a local crystalloid structure, so that a heat flow is transferred along a direction of the ordered molecular chain, which effectively inhibits the scattering of phonons in the S-LCER with high intrinsic thermal conductivity and greatly improves the intrinsic thermal conductivity of the S-LCER with high intrinsic thermal conductivity. According to polarized optical microscopy (POM) results, the S-LCEM behaves as a nematic liquid crystal with a mesomorphic range of 20° C. to 160° C. The S-LCER with high intrinsic thermal conductivity prepared by using the S-LCEM provided in the present disclosure as a raw material has a thermal conductivity of 0.33 W/m·K, which is significantly higher than that of ordinary epoxy resin (0.19 W/m·K), with an increase of 74%.

The preparation method provided in the present disclosure requires simple operations and is suitable for industrial production.

DETAILED DESCRIPTION

The present disclosure provides an S-LCEM with a structure shown in formula I:

formula I

Since the thermal conductivity of a solid depends on the diffusion of phonons, crystals and mesocrystals with an ordered structure can be adopted to increase the diffusion efficiency of phonons, thereby improving the thermal conductivity. There are biphenyl mesogenic groups with strong rigidity in a molecular structure of the S-LCEM provided in the present disclosure and there are also flexible connections among chain segments, which promotes the ordered arrangement of S-LCEM molecular chains during a curing process. The highly-ordered arrangement of such mesogenic units is conducive to the formation of a local crystalloid structure, so that a heat flow is transferred along a direction of the ordered molecular chain, which effectively inhibits the scattering of phonons in the S-LCER with high intrinsic thermal conductivity and greatly improves the intrinsic thermal conductivity of the S-LCER with high intrinsic thermal conductivity.

The present disclosure provides a method for preparing the S-LCEM according to the above technical solution, including the following steps:

mixing a compound $P_1$, 4-phenylphenol, a dehydrating agent, DMAP, and an organic solvent, and subjecting a resulting mixture to esterification to obtain a compound $P_2$;

mixing the compound $P_2$ with Amberlite IR-120 H ion-exchange resin and an organic solvent, and subjecting a resulting mixture to a first substitution reaction to obtain a compound $P_3$; and mixing the compound $P_3$ with ECH and TEA, and subjecting a resulting mixture to a second substitution reaction to obtain the S-LCEM; where, the compounds $P_1$, $P_2$, and $P_3$ have structural formulas as follows:

Compound $P_1$

Compound $P_2$

Compound P₃

In the present disclosure, all raw materials are commercially-available products well known to those skilled in the art unless otherwise specified.

In the present disclosure, a compound $P_1$, 4-phenylphenol, a dehydrating agent, DMAP, and an organic solvent are mixed, and a resulting mixture is subjected to esterification to obtain a compound $P_2$.

The present disclosure has no special limitations on a source of the compound $P_1$, which can be a commercially-available product well known to those skilled in the art or can be obtained by self-preparation. When the compound $P_1$ is provided by self-preparation, a preparation method of the compound $P_1$ may preferably include the following steps: mixing 2,2-dimethylolpropionic acid (DMPA), 2,2-dimethoxypropane (DMP), a catalyst, and an organic solvent, and subjecting a resulting mixture to alcoholysis to obtain the compound $P_1$.

In the present disclosure, the catalyst may preferably include p-toluenesulfonic acid monohydrate.

In the present disclosure, the DMPA, DMP, and catalyst may have a molar ratio preferably of 1:(1.0-1.6):(0.02-0.08), more preferably of 1:(1.2-1.5):(0.03-0.06), and most preferably of 1:(1.4-1.5):(0.04-0.05).

In the present disclosure, the organic solvent used for the alcoholysis may preferably include one or more of acetone, dichloromethane (DCM), and tetrahydrofuran (THF). When the organic solvent is a mixture of two or more organic solvents, the present disclosure has no special limitations on a volume ratio of the two or more organic solvents, and any ratio may be adopted. In the present disclosure, in the organic solvent, the DMPA may have a concentration preferably of 1.0 mol/L to 2.0 mol/L, more preferably of 1.2 mol/L to 1.8 mol/L, and most preferably of 1.4 mol/L to 1.5 mol/L.

In the present disclosure, the mixing of the DMPA, DMP, catalyst, and organic solvent may preferably include: subjecting the DMPA and the organic solvent to a first mixing to obtain a DMPA solution; subjecting the DMPA solution and the DMP to a second mixing to obtain a mixed solution; and subjecting the mixed solution and the catalyst to a third mixing. The present disclosure has no special limitations on a method for the first mixing, second mixing, and third mixing, and a mixing method well known in the art may be adopted, such as stirring. The present disclosure has no special limitations on speed and time of the stirring, provided that the components can be thoroughly mixed.

In the present disclosure, the alcoholysis may be conducted at a temperature preferably of 15° C. to 25° C. and more preferably of 20° C. to 25° C. In an example of the present disclosure, the alcoholysis may preferably be conducted at room temperature. In the present disclosure, the alcoholysis may be conducted preferably for 12 h to 24 h and more preferably for 18 h to 24 h. In the present disclosure, a reaction process for the alcoholysis may be shown in formula (1):

After the alcoholysis is completed, the present disclosure may preferably further include subjecting a reaction system obtained from the alcoholysis successively to a first concentration and extraction, subjecting an obtained organic phase successively to washing, desiccant drying, and solid-liquid separation, and subjecting an obtained liquid phase to a second concentration and vacuum drying to obtain the compound $P_1$. The present disclosure has no special limitations on a method for the first concentration, and a concentration method well known in the art may be adopted. In an example of the present disclosure, a method for the first concentration may preferably be rotary evaporation; the rotary evaporation may be conducted at a temperature preferably of 30° C. to 50° C. and more preferably of 35° C. to 45° C.; and the rotary evaporation may be conducted at a rotation speed preferably of 80 rpm to 100 rpm and more preferably of 85 rpm to 95 rpm. The first concentration is conducted to remove organic solvents in the reaction system. In the present disclosure, an extracting agent used for the extraction may preferably include DCM, trichloromethane (TCM), or cyclopentane. The present disclosure has no special limitations on an amount of the extracting agent and a process for the extraction, and an extracting agent amount and an extraction process well known in the art may be adopted. In the present disclosure, a method for the washing may preferably be water washing conducted preferably with distilled water. The present disclosure has no special limitations on the number of the water washings, and the water washing is conducted until a final washing liquid is neutral. In the present disclosure, the desiccant may preferably be anhydrous $Na_2SO_4$. The present disclosure has no special limitations on a method for the solid-liquid separation, provided that $Na_2SO_4$ can be removed by a solid-liquid separation method well known in the art, such as filtration or suction filtration. The present disclosure has no special limitations on a method for the second concentration, and a concentration method well known in the art may be adopted. In an example of the present disclosure, a method for the second concentration may preferably be rotary evaporation; the rotary evaporation may be conducted at a temperature preferably of 35° C. to 45° C. and more preferably of 38° C. to 42° C.; and the rotary evaporation may be conducted at a rotation speed preferably of 80 rpm to 100 rpm and more preferably of 85 rpm to 95 rpm. The second concentration is conducted to remove the extracting agent. The present disclosure has no special limitations on the vacuum drying, and vacuum drying conditions well known to those skilled in the art may be adopted.

In the present disclosure, after the compound $P_1$ is obtained, the compound $P_1$, 4-phenylphenol, dehydrating agent, DMAP, and organic solvent are mixed, and a resulting mixture is subjected to esterification to obtain a compound $P_2$.

In the present disclosure, the compound $P_1$, 4-phenylphenol, dehydrating agent, and DMAP may preferably have a molar ratio preferably of 1:(0.6-1.2):(0.6-1.2):(0.005-0.015) and more preferably of 1:(0.8-1.0):(0.8-1.0):(0.008-0.01). In the present disclosure, the dehydrating agent may preferably include one or more of dicyclohexylcarbodiimide (DCC), N,N'-diisopropylcarbodiimide (DIC), and N,N-carbonyldiimidazole (CDI). In the present disclosure, the DMAP is a catalyst.

In the present disclosure, the organic solvent used for the esterification may preferably include one or more of THF, DCM, and N,N-dimethylformamide (DMF). When the organic solvent is a mixture of two or more organic solvents, the present disclosure has no special limitations on a volume ratio of the two or more organic solvents, and any ratio may be adopted. In the present disclosure, in the organic solvent, the compound $P_1$ may have a concentration preferably of 0.5 mol/L to 1.0 mol/L and more preferably of 0.7 mol/L to 0.8 mol/L.

In the present disclosure, the mixing of the compound $P_1$, 4-phenylphenol, dehydrating agent, DMAP, and organic solvent may preferably include: subjecting the compound $P_1$, the 4-phenylphenol, and part of the organic solvent to a fourth mixing to obtain a compound $P_1$ mixture; subjecting the dehydrating agent, the DMAP, and the remaining organic solvent to a fifth mixing to obtain an adjuvant mixture; and subjecting the adjuvant mixture and the compound $P_1$ mixture to a sixth mixing. In the present disclosure, both the fourth mixing and the fifth mixing may further preferably be achieved by stirring. The present disclosure has no special limitations on a rate and time of the stirring, provided that all the components can be thoroughly mixed. In the present disclosure, the sixth mixing may further preferably be conducted as follows: adding the adjuvant mixture dropwise to the compound $P_1$ mixture at a speed preferably of 0.8 mL/min to 1.0 mL/min. The sixth mixing may be conducted at a temperature preferably of 0° C. to 5° C. and more preferably of 0° C. In the present disclosure, the part of the organic solvent and the remaining organic solvent may have a volume ratio preferably of 1:(0.8-1.0).

In the present disclosure, the esterification may be conducted at a temperature preferably of 15° C. to 30° C. and more preferably of 20° C. to 25° C.; and the esterification may be conducted preferably for 8 h to 12 h and more preferably for 10 h to 12 h. In the present disclosure, a reaction process for the esterification may be shown in formula (2):

formula (2)

After the esterification is completed, the present disclosure may preferably further include subjecting a reaction system obtained from the esterification to a second solid-liquid separation, subjecting an obtained liquid phase successively to a third concentration and extraction, subjecting an obtained organic phase successively to washing, desiccant drying, and a third solid-liquid separation, and subjecting an obtained liquid phase to a fourth concentration and vacuum drying to obtain the compound $P_2$. The present disclosure has no special limitations on a method for the second solid-liquid separation, and a solid-liquid separation method well known in the art may be adopted, such as filtration or suction filtration. The second solid-liquid separation is conducted to remove by-products of salts generated during the reaction. The present disclosure has no special limitations on a method for the third concentration, and a concentration method well known in the art may be adopted. In an example of the present disclosure, a method for the third concentration may preferably be rotary evaporation; the rotary evaporation may be conducted at a temperature preferably of 50° C. to 70° C. and more preferably of 55° C. to 60° C.; and the rotary evaporation may be conducted at a rotation speed preferably of 80 rpm to 100 rpm and more preferably of 85 rpm to 95 rpm. The third concentration is conducted to remove organic solvents in the reaction system. In the present disclosure, an extracting agent used for the extraction may preferably include DCM, TCM, or cyclopentane. The present disclosure has no special limitations on an amount of the extracting agent and a process for the extraction, and an extracting agent amount and an extraction process well known in the art may be adopted. In the present disclosure, the washing may preferably include washing successively with an alkaline solution and water; the alkaline solution may preferably include a $NaHCO_3$ aqueous solution or a $Na_2CO_3$ aqueous solution; the alkaline solution may have a mass percentage concentration preferably of 5% to 10%; and the water may preferably be distilled water. The present disclosure has no special limitations on the number of washings with the alkaline solution and water, provided that a final washing liquid obtained from washing with water is neutral. In the present disclosure, the desiccant may preferably be anhydrous $Na_2SO_4$. The present disclosure has no special limitations on a method for the third solid-liquid separation, provided that $Na_2SO_4$ can be removed by a solid-liquid separation method well known in the art, such as filtration or suction filtration. The present disclosure has no special limitations on a method for the fourth concentration, and a concentration method well known in the art may be adopted. In an example of the present disclosure, a method for the fourth concentration may preferably be rotary evaporation; the rotary evaporation may be conducted at a temperature preferably of 35° C. to 45° C. and more preferably of 38° C. to 42° C.; and the rotary evaporation may be conducted at a rotation speed preferably of 80 rpm to 100 rpm and more preferably of 85 rpm to 95 rpm. The fourth concentration is conducted to remove the extracting agent. The present disclosure has no special limitations on the vacuum drying, and drying conditions well known to those skilled in the art may be adopted.

After the compound $P_2$ is obtained, the compound $P_2$ is mixed with Amberlite IR-120 H ion-exchange resin and an organic solvent, and a resulting mixture is subjected to a first substitution reaction to obtain a compound $P_3$.

In the present disclosure, the organic solvent used for the first substitution reaction may preferably include one or more of methanol, THF, and acetone. When the organic solvent is a mixture of two or more organic solvents, the present disclosure has no special limitations on a volume ratio of the two or more organic solvents, and any ratio may be adopted. In the present disclosure, in the organic solvent, the compound $P_2$ may have a concentration preferably of 0.5 mol/L to 1.0 mol/L and more preferably of 0.7 mol/L to 0.8 mol/L.

In the present disclosure, the compound $P_2$ and the Amberlite IR-120 H ion-exchange resin may have a mass ratio preferably of 1:(0.4-0.6) and more preferably of 1:(0.4-0.5).

In the present disclosure, the mixing of the compound $P_2$, Amberlite IR-120 H ion-exchange resin, and the organic solvent may preferably be conducted as follows: subjecting the compound $P_2$ and the organic solvent to a seventh mixing to obtain a compound $P_2$ organic solution, and subjecting the compound $P_2$ organic solution and the Amberlite IR-120 H ion-exchange resin to an eighth mixing. In the present disclosure, both the seventh mixing and the eighth mixing may further preferably be achieved by stirring. The present disclosure has no special limitations on a rate and time of the stirring, provided that all the components can be thoroughly mixed.

In the present disclosure, the first substitution reaction may be conducted at a temperature preferably of 15° C. to 35° C. and more preferably of 20° C. to 25° C.; and the first substitution reaction may be conducted preferably for 10 h to 24 h and more preferably for 10 h to 12 h. In the present disclosure, a reaction process for the first substitution reaction may be shown in formula (3):

formula (3)

After the second substitution reaction is completed, the present disclosure may preferably further include subjecting a reaction system obtained from the second substitution to solid-liquid separation, and subjecting an obtained liquid phase successively to concentration and drying to obtain the compound $P_3$. The present disclosure has no special limitations on a method for the solid-liquid separation, and a solid-liquid separation method well known in the art may be adopted, such as filtration or suction filtration. The solid-liquid separation is conducted to remove unreacted Amberlite IR-120 H ion-exchange resin. The present disclosure has no special limitations on a method for the concentration, and a concentration method well known in the art may be adopted. In an example of the present disclosure, a method for the concentration may preferably be rotary evaporation; the rotary evaporation may be conducted at a temperature preferably of 50° C. to 70° C. and more preferably of 55° C. to 60° C.; and the rotary evaporation may be conducted at a rotation speed preferably of 80 rpm to 100 rpm and more preferably of 85 rpm to 95 rpm. The concentration is conducted to remove organic solvents in the reaction system. The present disclosure has no special limitations on a method for the drying, and a drying method well known in the art may be adopted. In an example of the present disclosure, the drying may preferably be vacuum drying. The present disclosure has no special limitations on the vacuum drying, and drying conditions well known to those skilled in the art may be adopted.

In the present disclosure, after the compound $P_3$ is obtained, the compound $P_3$ is mixed with ECH and TEA, and a resulting mixture is subjected to a second substitution reaction to obtain the S-LCEM.

In the present disclosure, the compound $P_3$, ECH, and TEA may have a molar ratio preferably of 1:(15-20):(2.5-3.0), more preferably of 1:(16-19):(2.6-2.9), and most preferably of 1:(17-18):(2.7-2.8).

In the present disclosure, the TEA serves as a catalyst for the reaction, provides an alkaline environment, and promotes the reaction of the compound $P_3$ and ECH. In the present disclosure, the ECH serves as both a reactant and a solvent.

In the present disclosure, the mixing of the compound $P_3$, ECH, and TEA may preferably be as follows: subjecting the compound $P_3$ and ECH to a ninth mixing to obtain a ninth mixture, and subjecting the ninth mixture and TEA to a tenth mixing. In the present disclosure, both the ninth mixing and the tenth mixing may further preferably be achieved by stirring. The present disclosure has no special limitations on a rate and time of the stirring, provided that all the components can be thoroughly mixed. In the present disclosure, the ninth mixing may be conducted at a temperature preferably of 50° C. to 60° C. and more preferably of 60° C.; and the ninth mixing may be conducted preferably for 35 min to 45 min. In the present disclosure, the mixing is conducted under the above conditions to make the compound $P_3$ fully dissolved in ECH. In the present disclosure, the tenth mixing may be conducted preferably at room temperature. In the present disclosure, the tenth mixing may preferably be conducted as follows: adding TEA dropwise to the ninth mixture. The present disclosure has no special limitations on a speed and time of the dropwise adding, and a dropwise adding rate and time well known to those skilled in the art may be adopted.

In the present disclosure, the second substitution reaction may be conducted at a temperature preferably of 15° C. to 35° C. and more preferably of 20° C. to 25° C.; and the second substitution reaction may be conducted preferably for 3 h to 8 h and more preferably for 3 h to 5 h. In the present disclosure, a reaction process for the second substitution reaction may be shown in formula (4):

formula (4)

In the present disclosure, after the second substitution reaction is completed, a reaction system obtained from the second substitution reaction may preferably be subjected successively to concentration and drying to obtain the S-LCEM.

The present disclosure has no special limitations on a method for the concentration, and a concentration method well known in the art may be adopted. In an example of the present disclosure, a method for the concentration may preferably be rotary evaporation; the rotary evaporation may be conducted at a temperature preferably of 65° C. to 75° C. and more preferably of 68° C. to 72° C.; and the rotary evaporation may be conducted at a rotation speed preferably of 80 rpm to 100 rpm and more preferably of 85 rpm to 95 rpm. The concentration is conducted to remove ECH and TEA in the reaction system.

The present disclosure has no special limitations on a method for the drying, and a drying method well known in the art may be adopted. In an example of the present disclosure, the drying may preferably be vacuum drying. The present disclosure has no special limitations on the vacuum drying, and drying conditions well known to those skilled in the art may be adopted.

The present disclosure also provides an S-LCER with high intrinsic thermal conductivity prepared by subjecting a mixture of an S-LCEM and an amine curing agent to curing reaction, where, the S-LCEM is the S-LCEM according to the above technical solution or an S-LCEM prepared by the preparation method according to the above technical solution; and the S-LCEM and the amine curing agent have a molar ratio preferably of 2:(1.0-1.2).

In the present disclosure, the S-LCEM and the amine curing agent may have a molar ratio preferably of 2:(1.0-1.15) and more preferably of 2:(1.0-1.1).

In the present disclosure, the amine curing agent may preferably include one or more of ethylenediamine (EDA), p-aminobenzenesulfonamide, 4,4'-diaminodiphenylmethane (DDM), and 4,4'-diaminodiphenylsulfone (DDS). When the amine curing agent is a mixture of two or more curing agents, the present disclosure has no special limitations on a ratio of the two or more curing agents, and any ratio may be adopted.

In the present disclosure, a preparation method of the S-LCER with high intrinsic thermal conductivity may preferably include the following steps:

mixing the S-LCEM and the amine curing agent, and subjecting a resulting mixture to curing reaction to obtain the S-LCER with high intrinsic thermal conductivity.

In the present disclosure, the mixing of the S-LCEM and the amine curing agent may preferably be conducted as follows: subjecting the S-LCEM to a first heating to obtain a hot S-LCEM; subjecting the amine curing agent to a second heating to obtain a molten curing agent; and mixing the hot S-LCEM and the molten curing agent. In the present disclosure, the mixing may preferably be conducted by stirring. The present disclosure has no special limitations on a rate and time of the stirring, provided that all the components can be thoroughly mixed.

In the present disclosure, the first heating may be conducted at a temperature preferably of 100° C. to 150° C., more preferably of 120° C. to 140° C., and most preferably of 120° C. to 130° C.

In the present disclosure, the second heating may be conducted at a temperature preferably of 100° C. to 150° C., more preferably of 120° C. to 140° C., and most preferably of 120° C. to 130° C.

In the present disclosure, the curing reaction may be conducted at a temperature preferably of 100° C. to 150° C., more preferably of 120° C. to 150° C., and most preferably of 130° C. to 140° C.; and the curing reaction may be conducted preferably for 2 h to 5 h and more preferably for 3 h to 4 h.

There are biphenyl mesogenic groups with strong rigidity in a molecular structure of the S-LCEM used in the present disclosure and there are also flexible connections among chain segments, which promotes the ordered arrangement of S-LCEM molecular chains during a curing process. The highly-ordered arrangement of such mesogenic units is conducive to the formation of a local crystalloid structure, so that a heat flow is transferred along a direction of the ordered molecular chain, which effectively inhibits the scattering of phonons in the S-LCER with high intrinsic thermal conductivity and greatly improves the intrinsic thermal conductivity of the S-LCER with high intrinsic thermal conductivity prepared by reaction of S-LCEMs with a curing agent.

The technical solutions of the present disclosure will be clearly and completely described below with reference to examples of the present disclosure. Apparently, the described examples are merely some rather than all of the examples of the present disclosure. All other examples obtained by a person of ordinary skill in the art based on the examples of the present disclosure without creative efforts shall fall within the protection scope of the present disclosure.

Example 1

10.0 g (74.6 mmol) of DMPA and 13.8 mL (111.8 mmol) of 2,2-dimethylpropane were dissolved in 50 mL of acetone, and a resulting mixture was thoroughly stirred; then 0.71 g (3.37 mmol) of p-toluenesulfonic acid monohydrate was added, and a resulting mixture was stirred at room temperature for 18 h; then 0.5 mL of TEA was added to the system and a resulting system was stirred for 5 min; after the reaction was completed, rotary evaporation was conducted to remove acetone, and extraction was conducted with DCM; and an obtained organic phase was washed with distilled water, dried with anhydrous $Na_2SO_4$, then subjected to rotary evaporation to remove DCM, and dried in a vacuum drying chamber to obtain a compound $P_1$.

5.0 g (28.7 mmol) of the compound $P_1$ and 4.9 g (28.7 mmol) of 4-phenylphenol were dissolved in 50 mL of THF to obtain a mixture; 5.9 g (28.7 mmol) of DCC and 35 mg (0.287 mmol) of DMAP were dissolved in 50 mL of THF, a resulting solution was slowly added dropwise to the above mixture at 0° C., and reaction was conducted at room temperature for 12 h; after the reaction was completed, a solid product was filtered out, and a filtrate was subjected to rotary evaporation to remove THF and then to extraction with DCM; and an obtained organic phase was washed with a $NaHCO_3$ aqueous solution and distilled water, then dried with anhydrous $Na_2SO_4$, filtered to remove $Na_2SO_4$, subjected to rotary evaporation to remove DCM, and dried in a vacuum drying chamber to obtain the compound $P_2$.

2.0 g (6.1 mmol) of the compound $P_2$ was dissolved in 50 mL of methanol, 1.0 g of Amberlite IR-120 H ion-exchange resin was added, and reaction was conducted at room temperature for 12 h; and after the reaction was completed, a resulting reaction solution was filtered to remove Amberlite IR-120 H ion-exchange resin, and a filtrate was subjected to rotary evaporation to remove methanol and then dried in a vacuum drying chamber to obtain a compound $P_3$.

2.0 g (7.0 mmol) of the compound $P_3$ was added to 20 mL of ECH, and a resulting mixture was stirred at 60° C. to make the compound fully dissolved; after a resulting solution was cooled to room temperature, 2.1 g (21.0 mmol) of TEA was added, and reaction was conducted for 3 h; after the reaction was completed, a resulting reaction solution was subjected to rotary evaporation to remove excess ECH and TEA and then dried in a vacuum drying chamber to obtain an S-LCEM.

Figure 1:
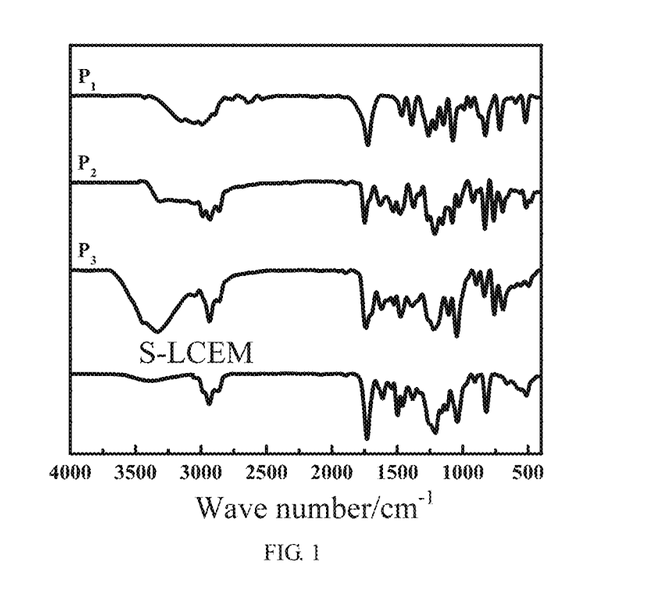
FIG. 1 shows infrared (IR) spectra of the compounds $P_1$, $P_2$ and $P_3$ and the S-LCEM prepared in Example 1.

The IR spectra of the compounds $P_1$, $P_2$ and $P_3$ and the S-LCEM prepared in this example are shown in FIG. 1. It can be seen from FIG. 1 that, for the compound $P_1$, a stretching vibration peak of methylene appears at 2,827 $cm^{-1}$ to 3,010 $cm^{-1}$, a stretching vibration peak at 1,724 $cm^{-1}$ is a characteristic peak of —C=O, and stretching vibration peaks at 1,145 $cm^{-1}$ and 1,076 $cm^{-1}$ are characteristic peaks of the —C—O— structure, which are consistent with the structure of compound $P_1$; for the compound $P_2$, characteristic peaks of benzene ring appear at 1,632 $cm^{-1}$ and 1,531 $cm^{-1}$, which is mainly attributed to the biphenyl group in a new monomer introduced by the reaction; for the compound $P_3$, a hydroxyl peak appears at 3,330 $cm^{-1}$, which is attributed to the formation of terminal hydroxyl in the reaction; and for the S-LCEM, the hydroxyl peak disappears, and a stretching vibration peak of epoxy group appears at 907 $cm^{-1}$, which is mainly attributed to a new epoxy group generated from the reaction of hydroxyl with ECH. It shows that an S-LCEM with a structure shown in formula I is prepared in the present disclosure.

Figure 2:
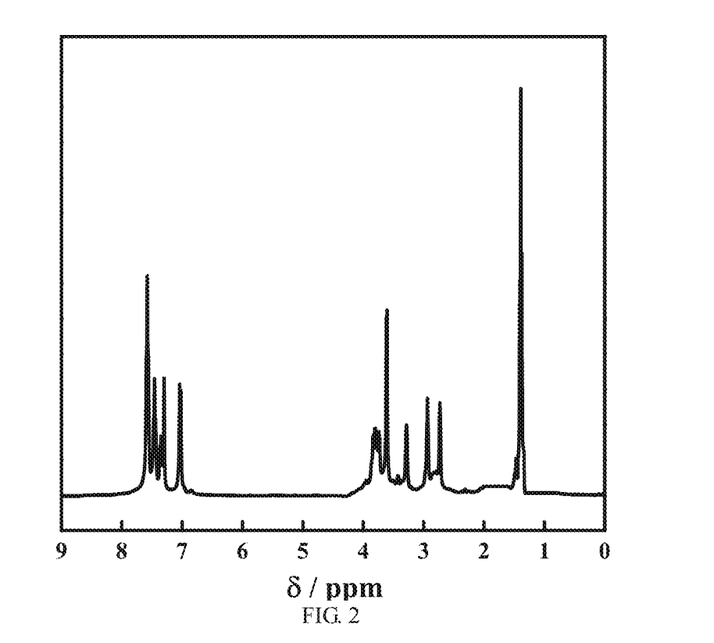
FIG. 2 is a $^1$H-nuclear magnetic resonance ($^1$H-NMR) spectrum of the S-LCEM prepared in Example 1.

A $^1H$ NMR spectrum of the S-LCEM prepared in this example is shown in FIG. 2. It can be seen from FIG. 2 that characteristic peaks of protons on a benzene ring appear at 7.6 ppm to 7.4 ppm and 7.0 ppm; the multiplets at 3.9 ppm to 3.7 ppm and 3.6 ppm to 3.5 ppm appear due to protons on two methylene groups; and chemical shifts of protons on an epoxy group appear at 3.3 ppm, 2.9 ppm, and 2.7 ppm. The chemical shifts are consistent with corresponding proton positions in the S-LCEM structure. Moreover, in combination with a peak area integral ratio, it can be known that the S-LCEM has a molecular structure shown in formula I.

Figure 3:
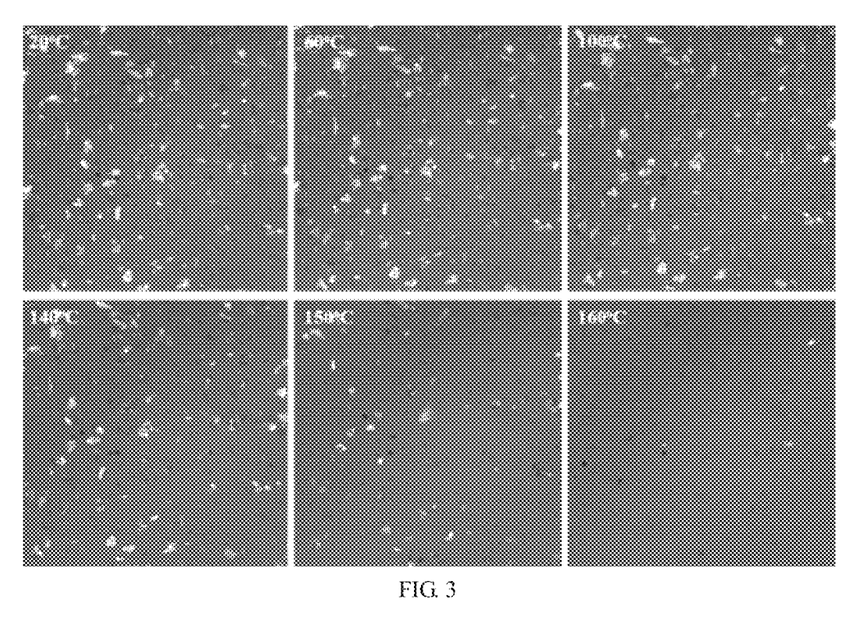
FIG. 3 shows POM images of the S-LCEM prepared in Example 1 at different temperatures.

A POM image of the S-LCEM prepared in this example is shown in FIG. 3. It can be seen from FIG. 3 that the S-LCEM exhibits liquid crystal properties at room temperature (20° C.). Specifically, an observation area has a bright field of view, many bright-yellow and blue spots are observed, and a liquid crystal phase is obvious, presenting a typical nematic liquid crystal morphology; when a temperature exceeds 140° C., the liquid crystal phase gradually disappears; and when the temperature further rises to 160° C., the liquid crystal phase almost completely disappears. It can be seen that the S-LCEM exhibits typical thermotropic liquid crystal properties, with a mesomorphic range of 20° C. to 160° C.

Figure 4:
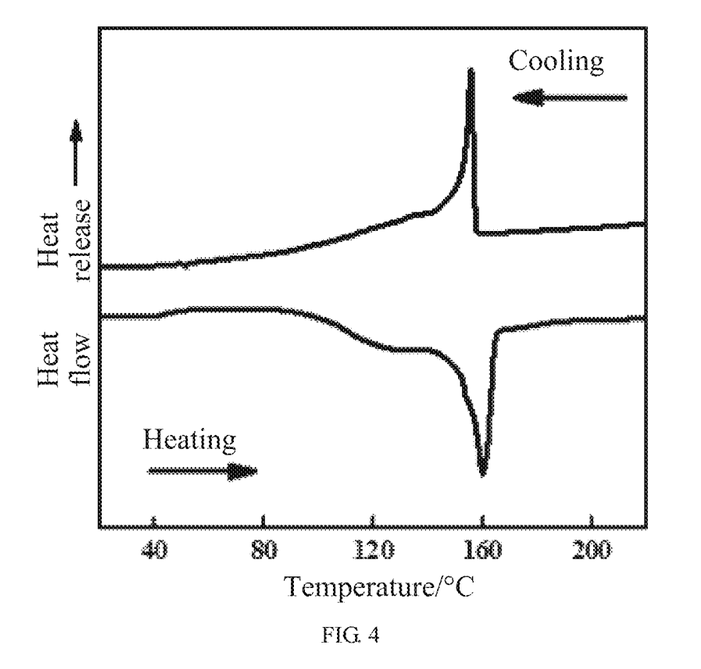
FIG. 4 shows a differential scanning calorimetry (DSC) curve of the S-LCEM prepared in Example 1.

A DSC curve of the S-LCEM prepared in this example is shown in FIG. 4. It can be seen from FIG. 4 that, during a heating process, the S-LCEM has an endothermic peak at 160° C., which is attributed to the transformation of the liquid crystal phase to an isotropic liquid phase. During a cooling process, the S-LCEM shows an exothermic peak at 156° C., indicating that the isotropic liquid phase is transformed into the liquid crystal phase at this temperature. DSC test results show that the LCE has a mesomorphic range of 20° C. to 160° C., which is consistent with POM test results.

Example 2

The S-LCEM was heated to 120° C., DDM was heated to 120° C. for melting and then added to the hot S-LCEM, and a resulting mixture was stirred thoroughly and then cured at 120° C. for 4 h to obtain the S-LCER with high intrinsic thermal conductivity, where, the S-LCEM and DDM had a molar ratio of 2:1.

Figure 5:
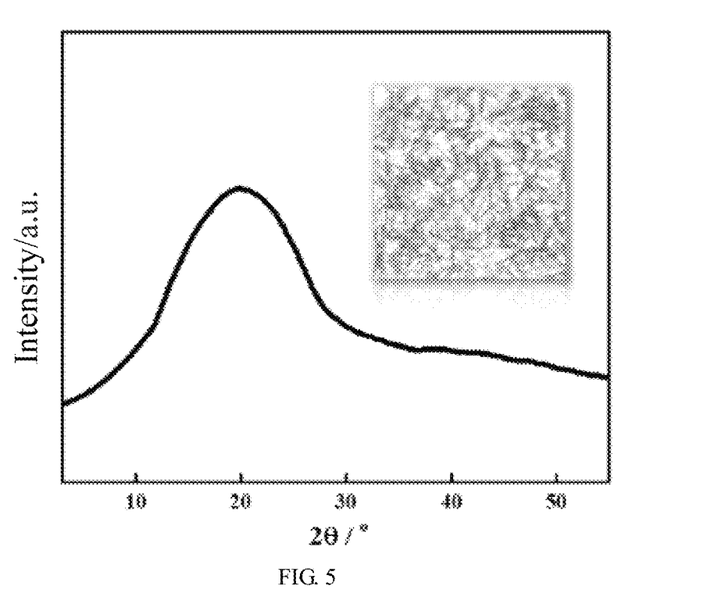
FIG. 5 shows an X-ray diffraction pattern and a POM image of the S-LCER with high intrinsic thermal conductivity prepared in Example 2, where, the interior image is the PLM image.

An X-ray diffraction pattern and a POM image of the S-LCER with high intrinsic thermal conductivity prepared in this example are shown in FIG. 5, where, the interior image is the POM image. It can be seen from FIG. 5 that the S-LCER with high intrinsic thermal conductivity only has a sharp and strong diffraction peak at 2θ=19.9° and birefringence is also observed in the POM image, both of which prove that the S-LCER with high intrinsic thermal conductivity retains the nematic liquid crystal morphology.

Figure 6:
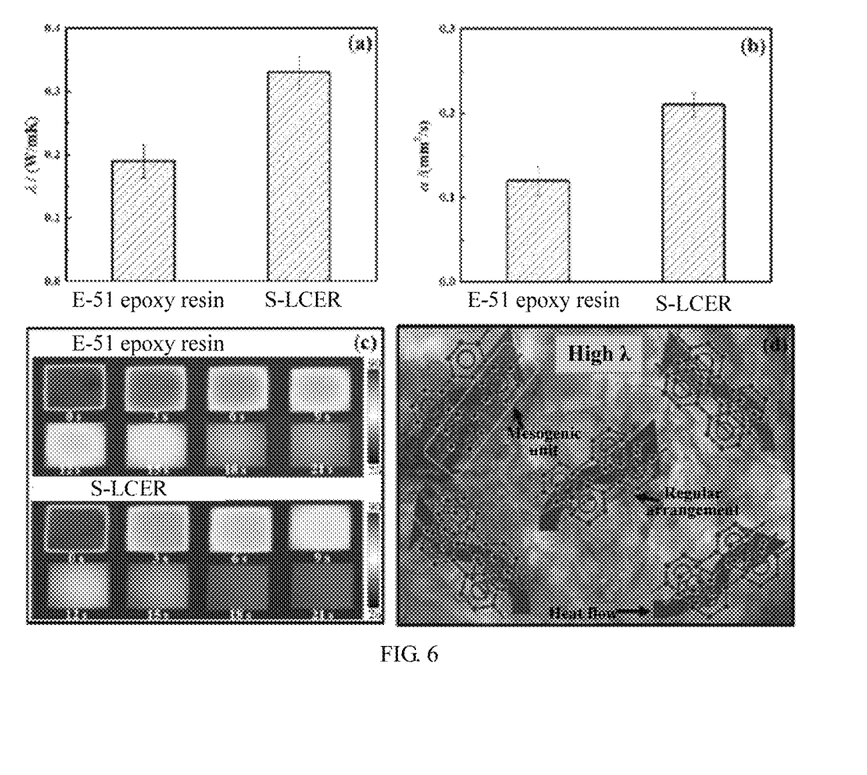
FIG. 6 is a schematic diagram illustrating the thermal conductivity $\lambda$, thermal diffusivity $\alpha$, IR thermal image, and thermal conduction of the S-LCER with high intrinsic thermal conductivity and bisphenol A epoxy resin E-51 prepared in Example 2, where, (a) shows the thermal conductivity $\lambda$, (b) shows the thermal diffusivity $\alpha$, (c) shows the IR thermal image, and (d) shows the thermal conduction.

A schematic diagram illustrating the thermal conductivity λ, thermal diffusivity α, IR thermal image, and thermal conduction of the S-LCER with high intrinsic thermal conductivity and bisphenol A epoxy resin E-51 prepared in this example is shown in FIG. 6, where, (a) shows the thermal conductivity λ, (b) shows the thermal diffusivity α, (c) shows the IR thermal image, and (d) shows the thermal conduction. It can be seen from FIG. 6 that the S-LCER with high intrinsic thermal conductivity prepared in the present disclosure has a thermal conductivity λ of 0.33 W/m·K, which is 74% higher than that of the bisphenol A epoxy resin E-51=0.19 W/m·K), and the S-LCER with high intrinsic thermal conductivity has a thermal diffusivity α of 0.21 $mm^2/s$, which is 75% higher than that of the bisphenol A epoxy resin E-51 (α=0.12 $mm^2/s$), indicating that the S-LCER with high intrinsic thermal conductivity prepared in the present disclosure exhibits superior intrinsic thermal conductivity. At the same heating time, the heat transfer and temperature rise of the S-LCER with high intrinsic thermal conductivity are faster than that of the bisphenol A epoxy resin E-51, further indicating that the S-LCER with high intrinsic thermal conductivity has superior intrinsic thermal conductivity. This is mainly because biphenyl mesogenic units with strong rigidity are introduced into the S-LCEM and the S-LCER with high intrinsic thermal conductivity still exhibits nematic liquid crystal properties. It further indicates that, in the S-LCER with high intrinsic thermal conductivity, high local orderliness is ensured while a cross-linked network is formed, thus promoting the formation of a local crystalloid structure. The molecular structure with regular arrangement can increase the heat transfer of lattice vibration (phonons) by inhibiting phonon scattering, as shown in the thermal conduction schematic diagram of (d), thereby increasing the thermal conductivity λ and the thermal diffusivity α of the S-LCER with high intrinsic thermal conductivity.

Example 3

The S-LCEM was heated to 150° C., DDS was heated to 150° C. for melting and then added to the hot S-LCEM, and a resulting mixture was stirred thoroughly and then cured at 150° C. for 5 h to obtain the S-LCER with high intrinsic thermal conductivity, where, the S-LCEM and DDS had a molar ratio of 2:1.2.

Figure 7:
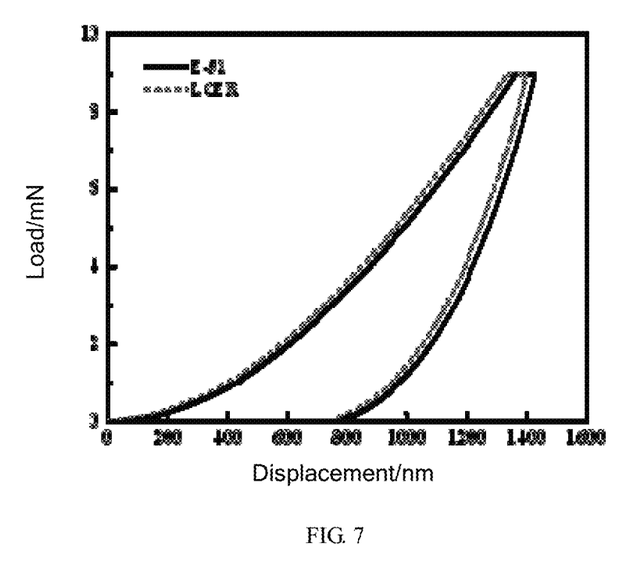
FIG. 7 shows load-displacement curves of the bisphenol A epoxy resin E-51 and LCER.

Load-displacement curves of the bisphenol A epoxy resin E-51 and LCER are shown in FIG. 7. It can be seen from FIG. 7 that, compared with the bisphenol A epoxy resin E-51, the LCER has a reduced indentation depth, indicating that the LCER has improved indentation resistance compared with the bisphenol A epoxy resin E-51.

Figure 8:
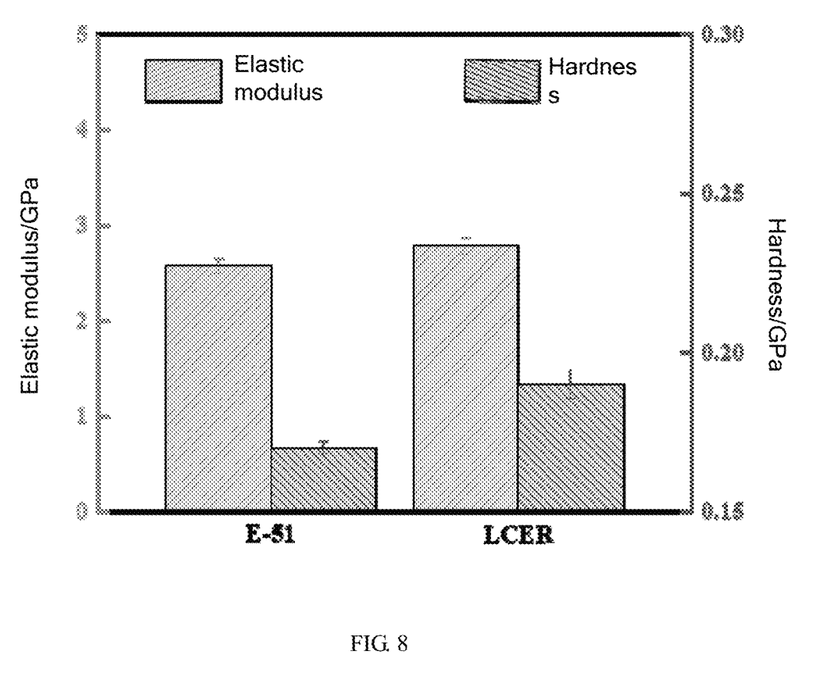
FIG. 8 shows an elastic modulus and a hardness of the bisphenol A epoxy resin E-51 and LCER.

An elastic modulus and a hardness of the bisphenol A epoxy resin E-51 and LCER are shown in FIG. 8. As shown in FIG. 8, the bisphenol A epoxy resin E-51 and LCER have elastic moduli of 2.57 GPa and 2.78 GPa, respectively, and the bisphenol A epoxy resin E-51 and LCER have hardness values of 0.17 GPa and 0.19 GPa, respectively. Compared with the bisphenol A epoxy resin, LCER has a higher elastic modulus and hardness, which is attributed to the more regular and compact connection and arrangement in LCER at the molecular scale.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A side chain liquid crystal epoxy monomer (S-LCEM) with a structure shown in formula I:

formula I

2. A method for preparing the S-LCEM according to claim 1, comprising the following steps:
   mixing a compound $P_1$, 4-phenylphenol, a dehydrating agent, 4-dimethylaminopyridine (DMAP), and an organic solvent, and subjecting a resulting mixture to esterification to obtain a compound $P_2$;
   mixing the compound $P_2$ with Amberlite IR-120 H ion-exchange resin and an organic solvent, and subjecting a resulting mixture to a first substitution reaction to obtain a compound $P_3$; and
   mixing the compound $P_3$ with epichlorohydrin (ECH) and triethylamine (TEA), and subjecting a resulting mixture to a second substitution reaction to obtain the S-LCEM;
   wherein,
   the compounds $P_1$, $P_2$, and $P_3$ have structural formulas as follows:

Compound $P_1$

Compound $P_2$

Compound $P_3$

3. The preparation method according to claim 2, wherein, the compound $P_1$, 4-phenylphenol, dehydrating agent, and DMAP have a molar ratio of 1:(0.8-1.0):(0.8-1.0):(0.008-0.01).

4. The preparation method according to claim 2, wherein, the esterification is conducted at 20° C. to 25° C. for 10 h to 12 h.

5. The preparation method according to claim 3, wherein, the esterification is conducted at 20° C. to 25° C. for 10 h to 12 h.

6. The preparation method according to claim 2, wherein, the compound $P_2$ and the Amberlite IR-120 H ion-exchange resin have a mass ratio of 1:(0.4-0.5).

7. The preparation method according to claim 2, wherein, the first substitution reaction is conducted at 20° C. to 25° C. for 10 h to 12 h.

8. The preparation method according to claim 6, wherein, the first substitution reaction is conducted at 20° C. to 25° C. for 10 h to 12 h.

9. The preparation method according to claim 2, wherein, the compound $P_3$, ECH, and TEA have a molar ratio of 1:(15-20):(2.5-3.0).

10. The preparation method according to claim 2, wherein, the second substitution reaction is conducted at 20° C. to 25° C. for 3 h to 5 h.

11. The preparation method according to claim 9, wherein, the second substitution reaction is conducted at 20° C. to 25° C. for 3 h to 5 h.

* * * * *